United States Patent [19]

Kievit et al.

[11] Patent Number: 4,515,595
[45] Date of Patent: May 7, 1985

[54] DISPOSABLE DIAPERS WITH ELASTICALLY CONTRACTIBLE WAISTBANDS

[75] Inventors: David J. Kievit, North College Hill; Thomas F. Osterhage, Green Township, Hamilton County, both of Ohio

[73] Assignee: The Procter & Gamble Company, Cincinnati, Ohio

[21] Appl. No.: 444,543

[22] Filed: Nov. 26, 1982

[51] Int. Cl.³ ............................................. A61F 13/20
[52] U.S. Cl. ............................................... 604/385 A
[58] Field of Search ............... 604/385, 386, 397, 398, 604/394

[56] References Cited

U.S. PATENT DOCUMENTS

| | | | |
|---|---|---|---|
| 2,545,216 | 3/1951 | Toussie | 604/394 |
| 3,639,917 | 2/1972 | Althouse | 2/270 |
| 3,819,401 | 6/1974 | Massengale et al. | 604/385 |
| 3,912,565 | 10/1975 | Koch et al. | 604/385 |
| 4,324,245 | 4/1982 | Mesek et al. | 604/385 |
| 4,337,771 | 7/1982 | Pieniak et al. | 604/385 |
| 4,352,355 | 10/1982 | Mesek et al. | 604/385 |

*Primary Examiner*—John D. Yasko
*Attorney, Agent, or Firm*—Monte D. Witte; Fredrick H. Braun; Richard C. Witte

[57] ABSTRACT

Disposable diapers having elasticized waistbands which allow the diapers to breathe and which reduce the incidence of waistband rollover. The waistbands are formed by affixing elastic elements between the topsheets and the backsheets (in the waistband region of the diapers) using regularly spaced, transversely extending regions of securement. Regions of nonsecurement are formed between pairs of the regions of securement thereby forming channels which allow the diaper to breathe and also forming corrugations which tend to inhibit waistband rollover.

5 Claims, 5 Drawing Figures

DISPOSABLE DIAPERS WITH ELASTICALLY CONTRACTIBLE WAISTBANDS

BACKGROUND OF THE INVENTION

1. Field of the Invention

This invention concerns disposable diapers, incontinent briefs, and the like having elastically contractible waistbands.

2. Background Art

Infants (and other incontinents) wear disposable diapers to receive and contain urine, feces, and other body fluids. Disposable diapers function both to contain the discharged materials and to isolate these materials from the body of the wearer and from the wearer's surroundings. Modern embodiments of disposable diapers frequently perform these tasks in a manner superior to that of traditional cloth diapers.

Disposable diapers normally comprise three elements: a liquid permeable topsheet designed to be placed next to the wearer's skin; a liquid impermeable backsheet which forms, in use, the outer surface of the diaper; and an absorbent element interposed between the topsheet and the backsheet.

The topsheet is frequently a hydrophobic non-woven fabric which is readily permeable to fluid. Its hydrophobicity tends to cause the surface in contact with the wearer's skin to be dry and protected from fluids absorbed within the absorbent element.

The absorbent element receives and retains fluids which pass through the topsheet. It normally comprises a batt of airlaid wood pulp fibers.

The backsheet functions to contain fluids within the absorbent element thereby protecting the wearer's outer garments and other surfaces from soiling by these fluids. Backsheets are commonly formed of fluid impermeable, vapor impermeable material such as polyethylene film.

Disposable diapers having many different basic designs are known to the art. For example, Duncan and Baker in U.S. Pat. No. Re. 26,152, issued Jan. 31, 1967, describe and claim a disposable diaper which has achieved wide acceptance and commercial success. Buell, in U.S. Pat. No. 3,860,003, issued Jan. 14, 1975, describes and claims another disposable diaper which, too, has achieved wide acceptance and commercial success. The diaper taught by Buell differs from that taught by Duncan and Baker in many respects, not the least of which is the provision in the Buell diaper of elasticized (or contractible) leg cuffs. Another embodiment of disposable diapers is described and claimed by Aziz and Blaney in European Patent Application No. 82200801.7, filed June 29, 1982. The Aziz and Blaney diaper also provides elasticized (or contractible) leg cuffs, but is of a somewhat different design than that described by Buell.

Mesek et al in U.S. Pat. No. 4,324,245, issued Apr. 13, 1982; Pieniak et al in U.S. Pat. No. 4,337,771, issued July 6, 1982; and Mesek et al in U.S. Pat. No. 4,352,355, issued Oct. 5, 1982 describe disposable diapers having elasticized cuffs and elasticized (or contractible) waistbands.

Strickland and Visscher in U.S. Pat. No. 4,253,461, issued on Mar. 3, 1981, describe and claim another form of disposable diaper sometimes referred to as an incontinent brief and intended to be worn by adults.

While the disposable diapers described above, particularly those described by Duncan and Baker, Buell, and Aziz and Blaney, function in exemplary manners, disposable diapers comprising fluid and vapor impermeable backsheets have sometimes been perceived as being somewhat hot and uncomfortable. Further, diapers provided with such impermeable backsheets are unable to self-dry as they otherwise would because evaporation of fluids from the absorbent element is precluded. To counteract this perception, and to permit self-drying, backsheets which are relatively impermeable to liquid but relatively permeable to vapor and which are known as breathable backsheets have been described. Breathable backsheets tend to provide a cooler garment and permit some measure of self-drying of the diaper while it is being worn. For example, Crowe, Jr. in U.S. Pat. No. 3,156,242, issued on Nov. 10, 1964, teaches the use of a microporous film as a breathable backsheet. Hartwell, in U.S. Pat. No. 3,881,489, issued on May 6, 1975, teaches a breathable backsheet comprising, in combination, two layers: a low-void volume perforated thermoplastic film and a porous high-void volume hydrophobic tissue. Sisson, in U.S. Pat. No. 3,989,867, issued on Nov. 2, 1976, teaches a breathable backsheet provided with tapered hollowed bosses which prevent the passage of liquid while allowing vapor to pass readily therethrough. Obenour, in U.S. Pat. No. 4,341,216, issued July 27, 1982, describes and claims a still different embodiment of a breathable backsheet.

The above cited ten patents and patent application are incorporated herein by reference.

While breathable backsheets do provide an improvement over the more common liquid and vapor impermeable backsheets, and while those described in the patents to Sisson, Hartwell and Obenour are of particular value, developments providing for more comfortable and more serviceable diapers have still been sought.

SUMMARY OF THE INVENTION

The present invention is of a disposable diaper comprising an elastically contractible waistband which allows the diaper to breath and which tends to resist waistband rollover. These benefits are achieved by providing disposable diapers with a waistband comprising an elastic element interposed between the topsheet and the backsheet and affixed to both the topsheet and the backsheet in such a way as to cause the formation of transverse channels between the topsheet and the elastic element. Transverse in this context means extending across ("transverse to") the waistband and that the channels which are formed between the topsheet and the elastic element and between the backsheet and the elastic element extend from the outer diaper margin to an interior region of the diaper.

DETAILED DESCRIPTION OF THE INVENTION

Figure 1:
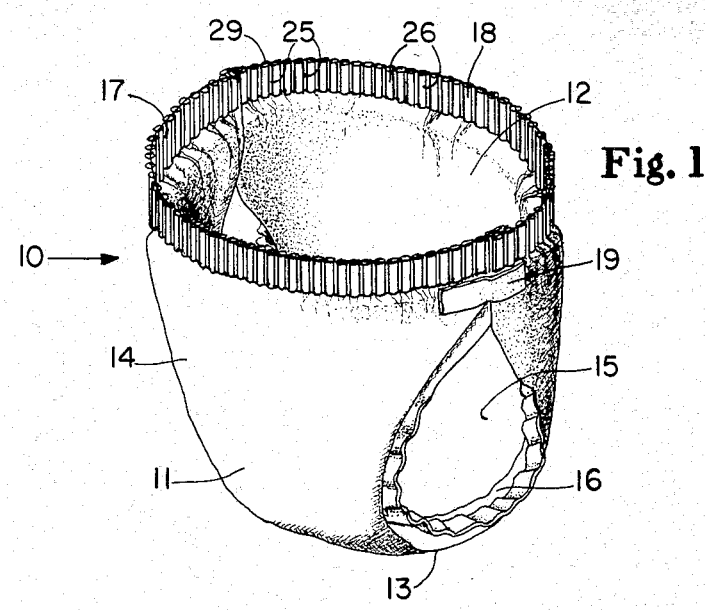
FIG. 1 is a perspective view of a disposable diaper embodying the present invention and in a configuration as applied to an infant.

While this specification concludes with claims particularly pointing out and distinctly claiming the subject matter regarded as the invention, it is believed that a better understanding of the invention can be achieved through careful reading of the following detailed description of the invention in conjunction with study of the attached drawings and the appended example.

Disposable diapers comprise three major elements: a topsheet; a backsheet; and an absorbent element. The topsheet forms the inside of the disposable diaper (i.e., that portion intended to be placed next to the wearer's skin). The backsheet generally forms the exterior surface of the disposable diaper. The absorbent element is interposed between the topsheet and the backsheet.

A disposable diaper is generally designed to be placed between and generally centered between the legs of an infant and secured about the infant by bringing the front portion of the diaper adjacent the front waist area of the infant and the rear portion of the diaper adjacent the rear waist area of the infant and securing the diaper in that position.

Optionally, disposable diapers comprise fastening tapes for securing the diaper about the infant. They also optionally comprise elastic members in the longitudinally extending margins to form an elastically contractible leg cuff or side flap. They also optionally comprise elastic elements in the laterally extending margins to form elastically contractible waistbands.

The waistband of a disposable diaper is that portion of the diaper which is intended to be placed adjacent the wearer's waist. While the waistband can comprise a separate element affixed to the body of the disposable diaper, it more often is an extension of other elements of the disposable diaper such as the backsheet or the topsheet or both the backsheet and the topsheet. Further, the waistband is generally considered to be that portion of the diaper extending from the laterally extending margin of the diaper to about the laterally extending margin of the absorbent element. Disposable diapers are normally constructed so as to have two waistbands: a front and rear. While disposable diapers can be constructed so as to have a single unitary waistband encircling the waist of the wearer, such designs are not preferred. It is also possible to construct a disposable diaper having three or more waistband sections intended to be affixed about the waist of the wearer, but, these embodiments, too, are not preferred.

The present invention provides a disposable diaper having at least one elastically contractible waistband. The waistband comprises an elastic element interposed between the topsheet and the backsheet and contractibly affixed to both the topsheet and the backsheet by transverse regions of securement. The transverse regions of securement, which are preferably essentially regularly spaced, define between each pair thereof a transverse region of nonsecurement extending from the outer margin of the waistband (which is the laterally extending margin of the diaper) essentially completely across the width of the elastic element. These transverse regions of nonsecurement exist between the topsheet and the elastic element and between the backsheet and the elastic element.

The phrase "contractibly affixed" means that the elastic element is affixed to the topsheet and to the backsheet when the elastic element is in an elongated orientation relative to its relaxed or contracted orientation and that when the elastic element is allowed to assume its relaxed or contracted orientation, the topsheet and the backsheet are gathered or shirred, usually in a regular, frequently predictable, manner.

FIG. 1 is a perspective view of a disposable diaper embodying the present invention. While the diaper illustrated in FIG. 1 is based on the disposable diaper design taught in the hereinbefore incorporated patent to Buell, and while this is a preferred diaper design for the use of the present invention, it must be realized that the present invention can be used, and is contemplated for use, with other disposable diaper designs. Several such designs are described in the hereinbefore incorporated patents and European patent application, but other designs can be readily envisioned by those skilled in the art. The Buell design has been selected to exemplify the present invention because it is a preferred design.

Referring now to FIG. 1, disposable diaper 10 is shown in perspective in a configuration as if it were applied about an infant. Disposable diaper 10 comprises a front portion 11 and a rear portion 12 with a crotch portion 13 interposed therebetween. In use, crotch portion 13 is placed between the legs of the infant and front portion 11 and rear portion 12 are placed, respectively, along the front and rear lower portions of the wearer's trunk. Topsheet 15 forms the inner surface of disposable diaper 10 while backsheet 14 forms its outer surface. Side flaps (or leg cuffs) 16 fit about the wearer's thighs. In use, front waistband 17 and rear waistband 18 are placed adjacent the wearer's waist regions on, respectively, the front and rear portions of the wearer's trunk. Disposable diaper 10 is held in position about the wearer by fastening tape 19. Outer margin of waistband 29 is shown in FIG. 1 as the upper edge of disposable diaper 10. Transverse regions of securement 25 and transverse regions of nonsecurement 26 in the waistbands are discussed more fully hereinafter.

It must be noted that reference numerals are used consistently throughout all the figures and that the thicknesses of certain materials in the figures have been exaggerated for clarity.

Figure 2:
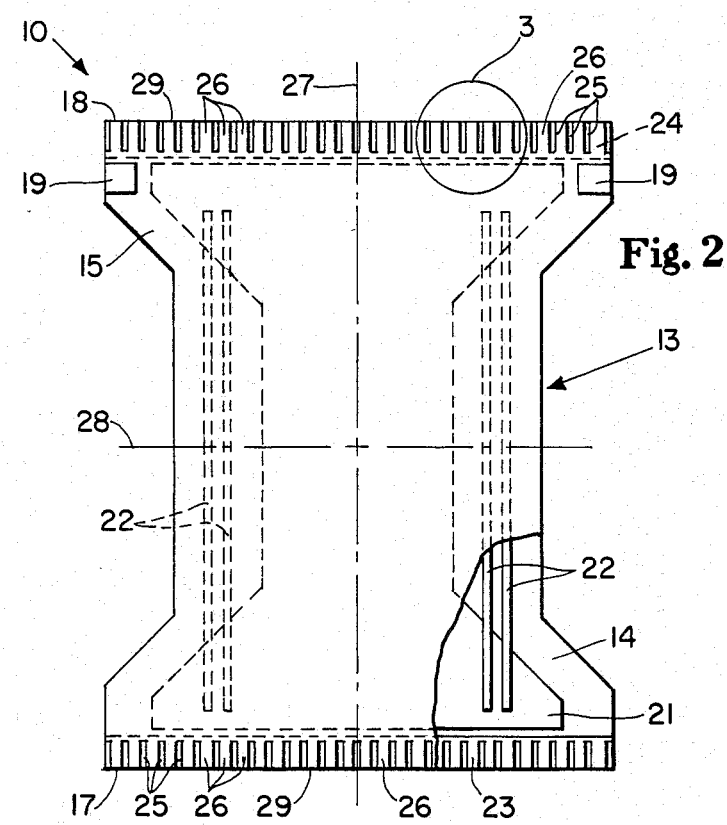
FIG. 2 is a partially fragmented plan view of the disposable diaper shown in FIG. 1 in an unfolded configuration.

FIG. 2 is a partially cut away plan view of disposable diaper 10 opened out into a planar configuration. Topsheet 15 is, in this illustration, the upper surface of the diaper while backsheet 14 is the lower surface. Absorbent element 21 is interposed between topsheet 15 and backsheet 14.

As illustrated, disposable diaper 10 is generally symmetrical about longitudinal center line 27 and lateral center line 28. While this is a preferred configuration, it is not necessary that disposable diaper 10 be symmetrical. An asymmetric orientation about lateral center line 28, as when crotch portion 13 is transposed toward front waistband 17, is quite useful.

Disposable diaper 10 is provided with elastic members 22 in the side margins thereof running generally parallel to longitudinal center line 27. In the embodiment illustrated, two elastic members 22 are placed on either side of disposable diaper 10; single or multiple elastic members can be used. The embodiment illustrated is, however, preferred.

Fastening tapes 19 are secured to disposable diaper 10 adjacent rear waistband 18.

Front elastic waist element 23 and rear elastic waist element 24 are positioned, respectively, in front waistband 17 and rear waistband 18 adjacent outer margin of waistband 29. In the embodiment illustrated in FIGS. 1 and 2, disposable diaper 10 comprises elastic waist elements in both the front and the rear waistbands. While this is a preferred embodiment, the present invention is useful in diaper designs having only the front or only the rear waistband elasticized.

Transverse regions of securement 25 and transverse regions of nonsecurement 26 are also illustrated in FIG. 2.

One major function of backsheet 14 is to prevent body fluids from escaping from disposable diaper 10 and soiling the wearer's outer garments and other surfaces in contact with the disposable diaper. Any compliant, non-irritating planar material which is impermeable to body fluids can be used as backsheet 14. Suitable materials are described with particularity in the hereinbefore incorporated patents and patent application. A preferred backsheet is formed from polyethylene film having a thickness of from about 0.012 to about 0.051 millimeter (mm).

Breathable backsheets (i.e., backsheets that permit the passage of vapor and air while retarding the passage of liquid) useful in the present invention are described in the hereinbefore incorporated patents to Crow, Jr., Hartwell, Sisson, and Obenour.

The size of backsheet 14 is dictated by the exact diaper design selected and the size of the infant intended to be the wearer; it can be readily ascertained by those skilled in the art.

Topsheet 15 can be any compliant, soft feeling, non-irritating (to the wearer's skin) planar material. It functions to contact the wearer's skin, to receive fluid discharges, to allow the discharges to pass readily therethrough into the absorbent element, and to isolate the wearer's skin from the fluids in the absorbent element. To aid in effective performance of the last function, the topsheet is preferably hydrophobic.

Topsheet 15 can be porous paper made from natural or synthetic fibers or mixtures thereof, non-woven fabric made from natural or synthetic fibers or mixtures thereof, apertured plastic film, porous foam, or the like. Examples of suitable topsheets are described in the hereinbefore incorporated patents and patent application.

A preferred topsheet is spun bonded non-woven polyester fabric made from fibers of from about 2.2 to about 2.5 denier, having a basis weight of about 17 grams (g) per square meter ($M^2$). Another preferred topsheet material has a basis weight of 22 g per $M^2$ and comprises about 65% (by weight) staple length, 1.5 denier polyester fibers (such as Kodel type 411 polyester fibers as sold by Tennessee Eastman Corporation, Kingsport, Tenn.); about 15% crimped, staple length, 1.5 denier rayon fibers; and about 20% acrylic copolymer binder (such as Celanese CPE 8335 as sold by Celanese Corporation of Charlotte, N.C.). "Staple length" refers to fibers having a length of at least about 15 mm.

Still another preferred topsheet is constructed from polypropylene fibers which have been carded and thermally bonded in a spaced-apart pattern. Fibers about 3.8 centimeters (cm) long and of from about 1.5 to about 3.0 denier are suitable. A preferred topsheet of this type has a basis weight of about 24 g per $M^2$.

Suitable topsheets can also be constructed from apertured plastic films such as those described by Radel and Thompson in U.S. Pat. No. 4,342,314, issued Aug. 3, 1982; Ferguson and Landrigan in U.S. Pat. No. 4,341,217, issued July 27, 1982; and Thompson in U.S. Pat. No. 3,929,135, issued Dec. 30, 1975. These three patents are incorporated herein by reference.

As with the case of backsheet 14, the size of topsheet 15 is dictated by the exact diaper design selected.

Absorbent element 21 can be any means which is generally compressible, conformable, non-irritating to the wearer's skin, and which is capable of absorbing and retaining fluids.

Absorbent element 21 can be constructed from any of a variety of materials commonly used in disposable absorbent articles and which are described in the hereinbefore incorporated patents. Examples of suitable absorbent materials include creped cellulose wadding, absorbent foams, absorbent sponges, super absorbent polymers, and, preferably, comminuted and airlaid wood pulp fibers commonly referred to as absorbent fluff. An absorbent fluff having a density of from about 0.05 to about 0.175 g per $cm^3$ is generally acceptable.

As in the case of backsheet 14 and topsheet 15, the size of absorbent element 21 is dictated by the exact diaper design selected.

Optionally, absorbent element 21 can have associated with either or both planar faces envelope tissues (not illustrated in the drawings) comprising any permeable material well known to those skilled in the art, such as wet strength tissue paper. When used, envelope tissues are generally coextensive with absorbent element 21 and either coterminus therewith or folded up and about the laterally extending margins thereof. Envelope tissues can optionally be secured to absorbent core 21 by any means well known to those skilled in the art.

Absorbent element 21 is interposed between backsheet 14 and topsheet 15. The diaper design selected determines whether or not the three elements are coterminus although, in general, either backsheet 14 or topsheet 15 or both extend beyond the margins of absorbent element 21. In the present invention, both backsheet 14 and topsheet 15 extend beyond the laterally extending margins of absorbent element 21 and are essentially coterminus along their laterally extending margins.

Optionally, backsheet 14 can be secured to absorbent element 21 by any convenient means (not illustrated in the drawings) well known to those skilled in the art. Examples of suitable means are parallel beads of adhesive (such as hot melt adhesive) and double sided adhesive tape; each extend essentially the entire longitudinal length of absorbent element 21.

Elastic members 22 serve to contract or gather the cuffs (longitudinally extending margins) of disposable diaper 10 and maintain them in contact with the legs of the wearer thereby providing improved fit and reducing fluid leakage from the diaper. One material which can be used for elastic elements 22 is an elastic tape having a cross section of about 0.18 mm by from about 1.5 mm to about 6.4 mm and made from natural rubber as available from East Hampton Rubber Company of Stuart, Va., under the trademark L-1900 Rubber Compound. Other suitable elastic members can be made from natural rubber elastic tapes sold under the trademarks Fulflex 9211 and Fulflex 9111 by Fulflex Company, of Scotland, N.C.

The length of elastic elements 22 is dictated by the precise diaper design chosen. In the design illustrated in FIGS. 1 and 2, elastic elements 22 extend a major portion of the longitudinal length of disposable diaper 10, but terminate outside the waist regions of disposable diaper 10.

Elastic members 22 are operably associated with disposable diaper 10 by securing them to the diaper adjacent its longitudinally extending margins by elastic attachment means which are not shown in the Figures. The elastic attachment means should be flexible and of sufficient adhesiveness to hold elastic members 22 in their stretched condition substantially indefinitely. One suitable means is hot melt adhesive. A more detailed description of the manner in which elastic members 22 should be positioned and secured to disposable diaper 10 is given in the hereinbefore incorporated patent to Buell.

Elastic members 22 are affixed to disposable diaper 10 in an elastically contractible condition so that in a normally unrestrained configuration elastic members 22 effectively contract or gather the diaper material adjacent elastic members 22. Elastic members 22 can be affixed to disposable diaper 10 in an elastically contractible condition in at least two ways. For example, elastic members 22 can be stretched to an elongated orientation and affixed to disposable diaper 10 while disposable diaper 10 is in an uncontracted condition. Alternatively, disposable diaper 10 can be contracted (in crotch portion 13, for example by pleating) and elastic members 22 can be affixed to the contracted disposable diaper 10 while the elastic members are in their relaxed or unstretched orientation.

Front waist element 23 and rear waist element 24 can be formed from the same materials as elastic members 22, but, at the option of the diaper designer, can be constructed of different materials. Preferably, elastic waist elements 23 and 24 are formed of elastic films having an elastic modulus of from about 3.5 to about 30 kilograms per $cm^2$. Examples of suitable materials include ABA block copolymers of polystyrene and polyolefin with alphamethyl styrene added. These materials are sold under the Kraton trademark by Shell Chemical Company of Houston, Tex. Still another example of suitable films are those formed from ethyl vinyl acetate by Exxon Chemical Company of Florham Park, N.J. Waist elastic elements 23 and 24 are at least about 0.6 cm wide, preferably at least about 1.6 cm wide. While the maximum width of the elastic waist elements 23 and 24 is determined by the diaper design and matters of economy, they generally are no wider than about 3.8 cm.

In the embodiment illustrated in FIGS. 1 and 2 elastic waist elements 23 and 24 each extend across essentially the entire lateral width of disposable diaper 10. While this is a preferred construction, the present invention is useful in designs wherein elastic waist elements 23 and 24 extend across only a portion of the lateral width of the diaper. Preferably, elastic waist elements 23 and 24 extend across a major portion of the lateral width of disposable diaper 10.

Elastic waist elements 23 and 24 are contractibly affixed to both the topsheet and the backsheet in front waistband 17 and rear waistband 18 by transverse regions of securement. Elastic waist elements 23 and 24 can be contractibly affixed in waistbands 17 and 18 by individually extending elastic waist elements 23 and 24 to elongated orientations, affixing elastic waist elements 23 and 24 to both topsheet 15 and backsheet 14 while topsheet 15 and backsheet 14 are in an uncontracted orientation, and allowing elastic waist elements 23 and 24 to assume their relaxed or contracted orientation.

Alternatively, elastic waist elements 23 and 24 can be formed from materials which contract unidirectionally and become elastic following specific treatment such as heating. Elastic materials are known which can be heated to their transition temperature and stretched into an elongated orientation. They are then chilled and become relatively inelastic and fixed in their elongated orientation. Subsequent heating causes the materials to contract to their initial (uncontracted or relaxed) orientation and to regain their elasticity. Examples of such materials are shown in U.S. Pat. No. 3,819,401, issued June 25, 1974 to Massengale et al and U.S. Pat. No. 3,912,565, issued Oct. 14, 1975 to Koch et al, both incorporated herein by reference. When such materials are used as elastic waist elements, the topsheet, backsheet, and the elastic waist element are affixed together by transverse regions of securement while all three are in uncontracted orientations. The system is then heated (as with heated air) and the elastic waist element is allowed to return to its relaxed or contracted orientation.

Transverse regions of securement 25 are shown in a generalized representation in FIGS. 1 and 2. More specific embodiments of transverse regions of securement 25 are depicted in FIGS. 3 and 4 which are enlarged views of a portion of rear waistband 18 indicated by reference numeral 3 in FIG. 2.

Figure 3:
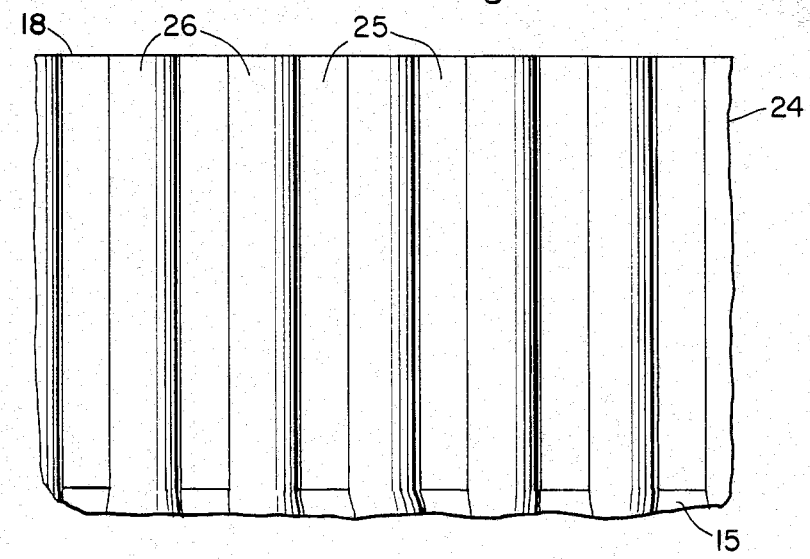
FIG. 3 is an enlarged partial view of the waistband of the diaper of FIG. 1 illustrating one embodiment of the present invention.
Figure 4:
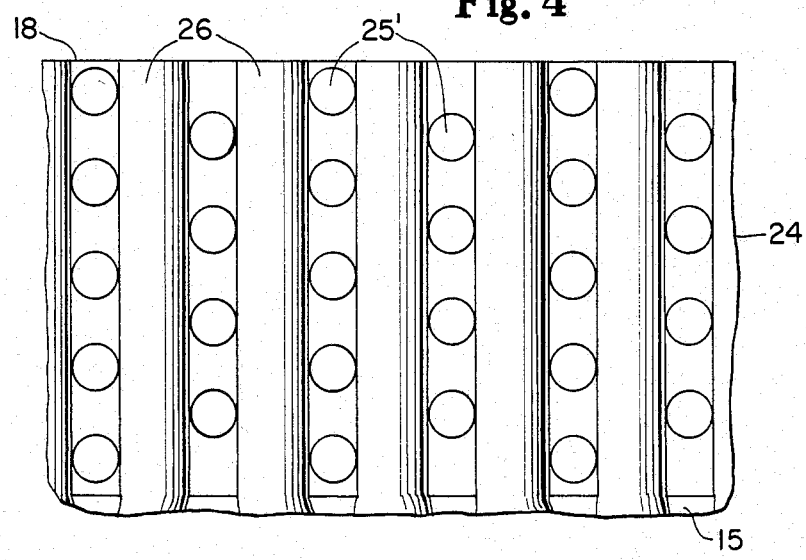
FIG. 4 is an enlarged partial view of the waistband of the diaper of FIG. 1 illustrating another embodiment of the present invention.

In this discussion of FIGS. 3 and 4, reference shall be made to rear waistband 18 and the components thereof. The same comments can be made about front waistband 17 and its components since the two waistbands can benefit from use of the present invention.

Transverse regions of securement 25 extend essentially across the whole width of elastic waist element 24.

The term "transverse" as used in this context refers to an orientation generally perpendicular to the major laterally extending dimension of waistband 18. That is to say, since rear waistband 18 extends laterally across the width of disposable diaper 10 and is generally parallel to lateral center line 28, the transverse regions of securement 25 extend across rear waistband 18 in an orientation essentially parallel to longitudinal center line 27; they are directed generally from outer margin of waistband 29 to the center of disposable diaper 10. As illustrated, transverse regions of securement 25 are shown to be at essentially right angles to lateral center line 28 and to the lateral extent of waistband 18. This is the preferred orientation. One can, however, depart from true transversity without departing from the scope and spirit of this invention. The departure from true (or absolute) transversity becomes too great when channels (as hereinafter discussed) are no longer formed extending essentially across the width of waistband 18. In general, departure from transversity becomes too great for practical operation of the present invention when the departure from transversity exceeds about 45° from true transversity (or perpendicularity to longitudinal center line 27).

The term "essentially across" is used in this context to indicate that transverse regions of securement 25 need not extend absolutely across the entire width of elastic waist element 24 so long as they extend sufficiently far across the width thereof to provide the channels discussed hereinafter.

In FIG. 3, transverse regions of securement 25 are shown as essentially regularly spaced unitary zones of sealing attaching elastic waist element 24 to topsheet 15 and backsheet 14 which is not visible in FIG. 3 or 4. The precise means for providing the zones of sealing can be readily selected by those skilled in the art. Examples include adhesive attachment, heat sealing, solvent sealing and the like. Preferably, ultrasonic welding is used.

Figure 5:
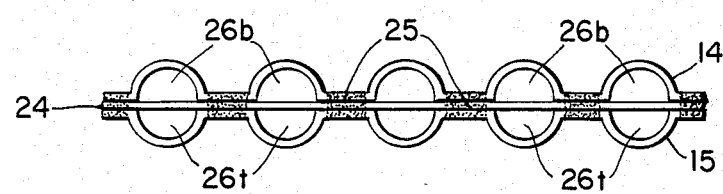
FIG. 5 is an end view of the portion of the waistband of the disposable diapers shown in FIGS. 3 and 4.

As illustrated in FIGS. 3, 4 and 5, the points of attachment of both topsheet 15 and backsheet 14 to elastic waist element 24 are in register (i.e. are coextensive). This is a preferred orientation, but the points of attachment of topsheet 15 to elastic waist element 24 can be offset from the adjacent points of attachment of backsheet 14 to elastic waist element 24. In such a situation there will be offset transverse regions of securement on either side of the elastic waist element.

FIG. 4 illustrates an alternate embodiment of transverse regions of securement 25'. In this embodiment, the transverse regions of securement comprise discrete spaced zones of sealing, preferably ultrasonic welds, effectively attaching the materials together and forming the channels hereinafter described. Preferably the discrete spaced zones are circular or elliptical.

Transverse regions of securement 25 can be from about 0.15 to about 1.0 cm wide (i.e. in the dimension generally parallel to lateral centerline 28. They are preferably regularly spaced, but they can be nonuniformly spaced. They are preferably from about 0.3 to about 1.5 cm apart as measured from center to center.

FIG. 5 illustrates the functioning of this invention. FIG. 5 is an end view of the portions of rear waistband 18 shown in FIG. 3 and FIG. 4 with rear elastic waist element 24 in a relaxed or contracted position. In FIG. 5, transverse regions of securement 25 are shown as darkened portions for emphasis. Since rear elastic waist element 24 is in its relaxed or contracted position, topsheet 15 and backsheet 14 are shown gathered. These gathers constitute and define transverse regions of nonsecurement 26b between backsheet 14 and rear elastic waist element 24 and transverse regions of nonsecurement 26t between topsheet 15 and rear elastic waist element 24. These transverse regions of nonsecurement 26b and 26t form open gathers or channels from the margin of the diaper extending to the interior of the diaper and terminating in the region adjacent the laterally extending edges of absorbent element 21. These open channels allow the diaper to breathe by allowing the exchange of air and vapor between the interior of the diaper and the surrounding atmosphere even when the diaper is secured about an infant.

When rear elastic waist element 24 is expanded to an elongated orientation, as when disposable diaper 10 is fastened about an infant, the channels decrease in size. This variation in size gives the person applying the diaper to the wearer some measure of control over the amount of breathability as by stretching the elasticized waistbands to greater or lesser extents when securing the diaper about the infant. Further, since open channels can occasionally allow liquid to leak from absorbent element 21, the ability to adjust the size of the channels gives some measure of control over the maximum extent of leakage which will be permitted.

At the same time as transverse regions of nonsecurement 26b and 26t are formed, topsheet 15 and backsheet 14 form structures in the nature of corrugations. These corrugations extend transversely across the width of rear waistband 18 tend to stiffen the waistband thereby tending to prevent waistband rollover (i.e., the bending of the waistband about itself).

EXAMPLE

Diapers according to the present invention were constructed following the basic design described in the aforementioned patent to Buell. This diaper design provided for two (front and rear) waistbands.

The absorbent element comprised absorbent fluff having a density of about 0.09 g per $cm^3$ and a basis weight of about 650 g per $M^2$. It was generally hourglass-shaped and was about 40 cm long, about 26.7 cm wide at each of its laterally extending margins, and about 9.5 cm wide in the crotch portion. It was symmetrical about its longitudinal center line, but asymmetrical about its lateral center line in that the crotch portion was centered about 21.1 cm from the rear lateral margin.

The topsheet comprised the thermally bonded polypropylene material hereinbefore mentioned and the backsheet 0.04 mm thick polyethylene film. Both also were hourglass-shaped and were about 45.1 cm long and about 31.8 cm wide at their laterally extending margins.

During construction, the absorbent element was interposed between the topsheet and the backsheet which were essentially coextensive and coterminus. Two-sided adhesive tapes running parallel to the longitudinal center line secured the backsheet to the absorbent element. They also secured the backsheet to the topsheet in the cuff regions, but not in the waistband regions.

The cuff portions of the diapers were elasticized by incorporating therein two elastic members in each longitudinally extending margin of the diaper at the crotch portion. Each was made of Fulflex 9111 and was 6.4 cm wide and 0.18 cm thick; the inner one was 13.3 cm long, the outer 15.2 cm. These elastic members were centered about the crotch portion. The pattern defined by the pair of members was centered about 11.7 cm from the longitudinal center line of the diaper and parallel thereto. The two elastic members in each diaper margin were centered on parallel lines about 1.6 cm apart.

Each diaper waistband extended the lateral width of the diaper and was about 31.8 cm long; each waistband was about 2.5 cm wide in the transverse direction. The elastic waist element used in each waistband was made by Clopay Corporation of Cincinnati, Ohio from a polystyrene-polyolefin block copolymer. Each was about 40.6 cm long, about 5.1 cm wide, and about 0.04 mm thick and was stretched to a length of about 49.5 cm prior to being secured to both the topsheet and the backsheet. At the time of securement the topsheet and the backsheet were in fully extended configurations.

Transverse regions of securement comprising discrete zones of ultrasonic welds were used to affix each elastic waist element to both the topsheet and to the backsheet. The transverse regions of securement each comprised six discrete elliptical zones of ultrasonic welds each having a major axis of about 1.5 mm and a minor axis of about 0.8 mm; each individual ellipse was set with its major axis at an angle of about 45° to the transverse direction. The transverse regions of securement were regularly spaced along each waistband and their centers were about 6.4 mm apart.

Adhesive fastening tapes were adhesively affixed to the diaper.

When worn by infants, these diapers performed in a satisfactory manner and the waistbands thereof tended to permit transfer of vapor from the interior of the diaper to the surrounding atmosphere and the corrugations formed in the waistband tended to prevent waistband rollover.

What is claimed is:

1. A disposable diaper having at least one waistband, said diaper comprising a topsheet, a backsheet, and an absorbent element interposed between said topsheet and said backsheet wherein at least one waistband comprises an elastic element interposed between said topsheet and said backsheet and contractibly affixed to said topsheet and to said backsheet by essentially regular transverse regions of securement defining therebetween transverse regions of nonsecurement extending from the outer margin of said waistband across essentially the entire width of said elastic element.

2. The diaper of claim 1 wherein said transverse regions of securement comprise unitary zones of sealing.

3. The diaper of claim 2 wherein said zones of sealing comprise ultrasonic welds.

4. The diaper of claim 1 wherein said transverse regions of securement comprise discrete, spaced apart zones of sealing.

5. The diaper of claim 4 wherein said zones of sealing comprise ultrasonic welds.

* * * * *